United States Patent [19]
Kojima et al.

[11] Patent Number: 5,310,713
[45] Date of Patent: May 10, 1994

[54] REGENERATION OF AN ALKYLATION CATALYST WITH HYDROGEN

[75] Inventors: Masami Kojima, Mt. Prospect; Joseph A. Kocal, Gurnee, both of Ill.

[73] Assignee: UOP, Des Plaines, Ill.

[21] Appl. No.: 43,954

[22] Filed: Apr. 5, 1993

[51] Int. Cl.$^5$ .................. B01J 20/20; B01J 23/96; B01J 27/32; B01J 38/58
[52] U.S. Cl. .......................... 502/30; 502/31; 502/32; 502/53; 585/721
[58] Field of Search ............. 502/53, 35, 30, 31, 502/32

[56] References Cited

U.S. PATENT DOCUMENTS

| | | | |
|---|---|---|---|
| 2,999,074 | 9/1961 | Block et al. | 252/442 |
| 3,318,820 | 5/1967 | Muller et al. | 252/415 |
| 3,352,941 | 11/1967 | Schoen et al. | 502/53 |
| 3,893,942 | 7/1975 | Yang | 502/53 |
| 4,098,833 | 7/1978 | Wristers | 260/666 |

*Primary Examiner*—Paul E. Konopka
*Attorney, Agent, or Firm*—Thomas K. McBride; Eugene I. Snyder

[57] ABSTRACT

Catalytic composites of the reaction product of a metal halide having Friedel-Crafts activity with the bound surface hydroxyl group of inorganic oxides and containing a zerovalent metal with hydrogenation activity, often are effective catalysts in motor fuel alkylation which, however, undergo rapid deactivation. Deactivated catalysts are readily regenerable by treating the composite from which alkylate feedstock has been removed with hydrogen at temperatures in the range of 10 to 300° C. Multiple regenerations are possible without appreciable activity loss.

10 Claims, No Drawings

REGENERATION OF AN ALKYLATION CATALYST WITH HYDROGEN

BACKGROUND OF THE INVENTION

Even in the era of anti-knock additives such as tetraethyl lead, the use of alkylate as a component in motor fuel gained both universal acceptance and importance. In the ensuing years alkylate has become an even more important component of motor fuel. Alkylate is an economical, clean-burning, high-octane, low volatility product that is becoming increasingly important as the composition of gasoline changes in response to environmental concerns and legislation. The governmental regulations most applicable to the increasing importance of alkylates are those affecting lead and butane. Adding lead anti-knock compounds was the easiest way to raise gasoline octane, but because of continuing concerns over the effects of lead emissions the phasing out of lead in gasoline was required, a process over 90% complete. Butane is another effective octane-booster but tends to evaporate from gasoline, especially in warm weather, contributing to smog formation. Recent EPA regulations have effected their virtually complete removal from gasoline.

The term "alkylate" generally refers to a complex mixture resulting from the alkylation of olefins present or formed in a feedstream of C2–C6 olefim with intermediates arising primarily from alkanes, especially branched alkanes, and predominantly those with 4 carbon atoms, especially isobutane, also present in the same feedstream. It is most desirable that the complex product mixture referred to as alkylate contains predominantly trimethylpentanes, since these are high-octane components which add considerable value to motor fuel, yet the chemistry of alkylation affords a dazzling variety of products resulting from only a few basic chemical reactions characteristic of the carbonium ion which plays a central role in the alkylation process. Thus, chain transfer (intermolecular hydride transfer and alkyl shifts), ohgomerization and disproportionation serve to place into the alkylate as byproduct materials of from 5–12± carbon atoms from a feed containing only C4 olefim and alkanes.

The alkylation of olefins is catalyzed by strong acids generally. Although such alkylation has been the focus of intense and continuing scrutiny for several decades, the requirements of optimum selectivity while achieving high conversion have heretofore narrowed, for all practical purposes, the commercial choice of catalyst to sulfuric acid and liquid hydrogen fluoride. Vile processes based on each of these acids have gained commercial acceptance those based on HF have been favored at least in part because of the relative ease of HF regeneration. A brief but valuable overview of HF-catalyzed alkylation is presented by B.R. Shah in "Handbook of Petroleum Refining Processes", R.A. Meyers, editor, McGraw-Hill Book Company, 1986, pp 1-3 through 1-28.

In a rather over-simplified description, the HF-catalyzed alkylation process is carried out as follows. Olefinic and isobutane feedstocks are combined and mixed with BF in an alkylation reaction zone. The reactor effluent is separated into the desired alkylate, acid, and other light gases which are predominantly unreacted isobutanes. The HF is either recycled to the reactor directly or regenerated, in whole or in part, prior to its being recycled to the reactor. Unreacted isobutane also is recycled to the reactor, and the alkylate is then used in motor fuel blending.

Recently HF (hydrofluoric acid) has come under enviroriinental pressure. Hydrofluoric add is classified as an Acutely Hazardous Material, and in Southern California the Board of the South Coast Air Quality Management District recently required that the use of HF in alkylation be phased out by January 1, 1998. Consequently there is increasing reason to seek substitutes for HF as an alkylation catalyst for alkylate production. It is quite desirable to have a solid acid as an effective catalyst, for this permits development of fixed bed processes, a desirable alterative in the petroleum refining industry.

One of the promising solid catalysts for alkylation of C2–6 olefins with alkanes in the 4 to 6 carbon range, a process hereafter specifically referred to as motor fuel alkylation, is the reaction product between one or more of the metal halides active as Friedel-Crafts catalysts and a refractory inorganic oxide having surface hydroxyl groups, where the refractory inorganic oxide also contains dispersed thereon a metal having hydrogenation activity for olefins. Such catalysts are reasonably well known in the art, as exemplified by U.S. Pat. No. 2,999,074, and includes, for example, the reaction product of aluminum chloride and alumina containing zerovalent platinum. As is commonly the case, these catalysts deactivate with use, where the deactivation is measured by the percent conversion of olefins, and it is imperative to have means of repeatedly regenerating these catalysts, i.e., to restore their activity, in order to utilize their catalytic effectiveness over long periods of time. It is further desirable that the method of regeneration be minimally disruptive to the motor fuel alkylation process itself. By that is meant that it is most desirable that the catalyst not be subjected to conditions or agents foreign to those of the alkylation process itself. It is still further desirable to minimize the regeneration cycle time relative to the alkylation cycle time. That is, if the complete process cycle time be the sum of the time during which the catalyst is used in alkylation (alkylation cycle time) and the time during which the catalyst is regenerated (regeneration cycle time) one desires that the latter be as short as possible. Of course the ideal regeneration cycle time is zero, but this corresponds to the case where the catalyst does not deactivate which, unfortunately, is contrary to experience.

We have developed a simple yet effective method of regenerating a deactivated catalyst which satisfies both of the foregoing criteria. More particularly, it is found that after removing liquid hydrocarbons from the deactivated catalyst, treatment of the catalyst with hydrogen at approximately the same pressure as that used during alkylation and at reasonably low temperatures affords virtually complete regeneration, often with increased product quality. Our method is simple, very effective both in restoring activity and affording multiple regenerations, and requires a cycle time which is commercially feasible. U.S. Pat. No. 4,098,833 relates to regeneration of a catalyst of a metal halide and a Bronsted acid containing fluorine, where the deactivated catalyst may have been used as an alkylation catalyst, using hydrogen and a separate noble metal hydrogenation component. The patentee's catalyst is different from that here in many respects, including the fact that his catalyst is unsupported, is liquid, and always includes a fluorine-containing Bronsted acid.

Muller et al. in U.S. Pat. No. 3,318,820 describe regeneration of an isomerization catalyst consisting essentially of the reaction product of aluminum halide and hydroxyl groups of surface-hydroxyl-containing adsorbent solid, such as alumina and silica, by treatment with hydrogen followed by treatment with gaseous HCl. No noble metal hydrogenation component is mentioned, and post-hydrogen treatment with HCl is an essential part of the regeneration process.

SUMMARY OF THE INVENTION

The purpose of our invention is to repeatedly restore the activity of catalysts of metal halides reacted with surface hydroxyl groups of refractory inorganic oxides and which also contain small amounts of a metal active in hydrogenation where such catalysts have become deactivated in use as a motor fuel liquid phase alkylation catalyst. One embodiment comprises treating the catalyst freed of all liquid phase with hydrogen at a temperature in the range of 10–300° C. and at a hydrogen partial pressure in the range of 1–150 atmospheres. In a more specific embodiment the refractory inorganic oxide is alumina. In another specific embodiment the metal halide is aluminum chloride. In a still more specific embodiment the metal halide is aluminum chloride, the refractory inorganic oxide is alumina, and the metal having hydrogenation activity is platinum. In another embodiment the catalyst is treated with hydrogen at the aforementioned temperature and pressure and in the presence of liquid isobutane and a chloride source. Other embodiments will be apparent from the description which follows.

DESCRIPTION OF THE INVENTION

Although the group of catalysts which may be characterized as the reaction products of a Friedel-Crafts active metal halide and surface hydroxyl groups of inorganic oxides and which additionally contains a zerovalent metal having hydrogenation activity shows promise in the liquid phase alkylation of alkenes with alkanes to produce alkylates valuable as a component of motor fuel, such catalysts deactivate quickly. Therefore there is a need to develop a method of regenerating the catalyst, preferably by procedures which are relatively simple, which are inexpensive, and which are effective in restoring catalytic activity over many multiple regeneration cycles. This application describes such a method, which is to free the catalyst of the liquid phase reaction mixture and then treat the catalysts with hydrogen at temperatures of at least 10° C. up to about 300° C. and at a hydrogen partial pressure at least about 1 to about 150 atmospheres. Treatment of the catalyst with hydrogen may be effected with either liquid-free catalysts or in the presence of liquid isobutane and a chloride source.

Because the catalysts of this invention are well known in the art (see U.S. Pat. No. 2,999,074; cf 3,318,820) it is not necessary to describe them here at great length, accordingly the following description will merely suffice to afford the reader an understanding of our invention. The refractory inorganic oxides suitable for use in this invention have a surface area of at least about 35 m$^2$/g, preferably greater than about 50 m$^2$/g, and more desirably greater than 100 m$^2$/g. There appears to be some advantage to working with materials having as high a surface area as possible, although some exceptions also are known. Suitable refractory inorganic oxides include alumina, titania, zirconia, chromia, silica, boria, silica-alumina, aluminum phosphate, and combinations thereof. Of these alumina is particularly preferred. Any alumina phase may be used so long as it has a surface area of at least 35 m$^2$/g and has surface hydroxyl groups, which for all practical matters excludes alpha-alumina, although the various phases are not necessarily equivalent in their effectiveness as a motor fuel alkylation catalyst.

It is required that the refractory inorganic oxide have surface hydroxyl groups, by which is meant not adsorbed water but rather hydroxyl (OH) groups whose oxygen is bound to the metal of the inorganic oxide. These latter hydroxyl groups sometimes have been referred to as chemically combined hydroxyl. Since the presence of adsorbed water is generally detrimental to the preparation of the catalysts of our invention, the refractory inorganic oxides are first treated to remove surface hydroxyl groups from water, most usually by calcination at a temperature which specifically and preferentially removes physically adsorbed water without chemically altering the other hydroxyl groups. For example, temperatures ranging from about 350° C. to about 700° C. are usually satisfactory where the inorganic oxide is alumina.

A zerovalent metal having hydrogenation activity generally is deposited on the refractory inorganic oxide prior to the reaction of its surface hydroxyl groups with metal halides. Although such a procedure has proven both convenient and effective, we do not wish to imply that this is the only sequence which may be used to afford an effective catalyst. Metals which have been found to be particularly effective include nickel and the noble metals of platinum, palladium, ruthenium, rhodium, osmium, and iridium, although platinum and palladium are by far the most desirable of the noble metals. The desired metal may be composited with the refractory inorganic oxide in any desired manner, such as by impregnation, coprecipitation, dipping, and so forth. Such methods are well known and need not be described here. Metal levels may range between about 0.01 up to about 1.0 weight percent for the noble metals, based on the weight of the finished catalyst, and from about 0.1 up to about 5 weight percent for nickel. The composite of the metal and refractory inorganic oxide is dried and calcined under controlled conditions to remove physically adsorbed water but under sufficiently mild conditions so that the "chemically combined" hydroxyl groups are not eliminated.

Subsequent to metal deposition and calcination, the surface hydroxyl groups of the refractory inorganic oxide are reacted with a metal halide having Frieder-Crafts activity. Among the metals which may be used are included aluminum, zirconium4 tin, tantalum, titanium, gallium, antimony, phosphorous, and boron. Suitable halides are the fluorides, chlorides, and bromides. Representative of such metal halides include aluminum chloride, aluminum bromide, ferric chloride, ferric bromide, zirconium chloride, zirconium bromide, boron trifluoride, titanium tetrachloride, gallium chloride, tin tetrachloride, antimony fluoride, tantalum chloride, tantalum fluoride, phosphoms chloride, phosphorus fluoride, and so forth. Of these metal halides the aluminum halides are preferred, especially aluminum chloride. Except for boron trifluoride, the chlorides are generally the preferable halides.

The reaction between the metal halides of this invention and the surface hydroxyl groups of the refractory inorganic oxide is readily accomplished by, for example, sublimation or distillation of the metal halide onto the surface of the particles of the metal-inorganic oxide composite. The reaction is attended by the elimination of between about 0.5 and 2.0 moles of hydrogen halide per mole of metal halide adsorbed thereon. The reaction temperature will depend upon such variables as the reactivity of metal halides and its sublimation temperature or boiling point, where the metal halide is reacted in the gas phase, as well as on the nature of the refractory inorganic oxide. For example, using aluminum chloride and alumina as our specific examples reaction readily occurs within the range between about 190° through 600° C.

We have found the following method to be very effective in restoring lost activity to the catalyst and to be effective over many regeneration cycles. It is first necessary to remove all of the liquid reaction mixture from the catalyst, which can be done quite simply by draining all of the liquid phase from the catalyst. After the liquid phase is removed the catalyst is treated with hydrogen at a partial pressure between about 1 up to about 2,000 psi. The temperature at which the catalyst is treated with hydrogen varies between about 10 and about 300° C. Regeneration time depends inversely with temperature. Consequently, higher temperatures are favored if a shorter regeneration time is desirable, and for this reason temperatures even higher than 300° C. may be used although these are not generally recommended. However, other factors favor low temperatures regeneration. Regeneration at alkylation process conditions is most desirable in order to eliminate the costs of heating and cooling, and to make regeneration operationally simpler and easier. In fact, regeneration is preferably done in the temperature range between about 10 and about 200° C., for which a regeneration time on the order of 6 hours suffices to effect m restoration of activity.

The following examples are merely illustrative of our invention and are not intended to it in any way.

General Procedure

Typical test conditions included a temperature of 10° C., a reaction pressure of 450 psig, a butene-2 LHSV of 0.2 hr$^{-1}$ with an isobutane/butene mole ratio of 100, 75, 45, or 20. Alkylation was performed in the presence of 2,000 ppm chloride (as butyl chloride) and with hydrogen present at 0.25 mole proportions relative to butene.

Catalyst regeneration with hydrogen was performed as follows. At the end of a process cycle (i.e., when catalyst had appreciably deactivated) a stream of isobutane was introduced at 1 LHSV and the isobutane/olefin feedstock was cut out. After two hours of flushing at 10° C., the system was depressurized to 1 atmosphere, after which hydrogen was introduced along with 10-1000 ppm of chloride as butyl chloride and the system pressurized to 450 psig. The temperature was raised to 200° C. and maintained at that temperature for 4 hours, after which the reactor was cooled to 10° C. over approximately 2 hours and then rifled and flushed with isobutane for an additional 1-2 hours. The entire procedure lasted approximately 10 hours.

EXAMPLE 1

Regeneration with pure hydrogen. A catalyst was prepared containing 0.25 weight percent platinum on 1/16" gamma alumina extrudates on which had been sublimed aluminum chloride in an amount corresponding to 0.75 weight percent Al. (Aluminum content was not measured directly, but rather was determined on the basis of chloride content.) The catalyst then was treated with a chloride source so that it initially contained chloride in the range of 3-7 weight percent, where suitable chloride sources include an alkyl chloride or hydrogen chloride. This catalyst was used in motor fuel alkylation under the conditions stated above and regenerated as described above for 10 process cycles. There was no observable activity loss between cycles 2 and 10, all of which were conducted at an isobutane/butene ratio of 45. The average alkylate product calculated research octane number (RON) was about 89 for all cycles.

A control was run using the same catalyst except without platinum. No regeneration was observed; the catalyst after hydrogen treatment continued to deactivate unabated without any measurable restoration of activity.

Similar experiments were conducted using gallium chloride, $GaCl_3$, in place of aluminum chloride. Although regeneration tests were not so extensive the deactivated catalyst was completely regenerated under the conditions described above. The product akylate showed an RON of 90.5.

In another run palladium at 0.5 weight percent replaced the platinum in an aluminum chloride-alumina catalyst. The regeneration was successfully performed and the average alkylate product RON was about 88.5.

EXAMPLE 2

Regeneration with isobutane, butyl chloride, and hydrogen. Because chloride loss is observed from catalysts when regeneration is done in an isobutane-hydrogen stream with subsequent deactivation of the catalyst, it is highly desirable to perform the regeneration in the presence of an organic chloride, such as butyl chloride. In these regenerations isobutane containing 1,000 ppm chloride (as butyl chloride) and hydrogen cofed at 1 standard cubic foot an hour were cut in at the end of the process cycle at the same time that feed blend was cut out. After a two-hour flush the pressure was raised to 600 psig and the temperature was raised to about 135°0 C. and maintained there for 12 hours. After the catalyst composite was cooled to 10° C., the feed blend was cut in and the regeneration gas stream was cut out. The entire procedure typically took 16-18 hours.

A catalyst of aluminum chloride on gamma alumina extrudates containing 0.25 weight percent platinum was readily regenerated under the aforementioned conditions to afford an alkylate product of average RON of 90.5. Where butyl chloride was absent from the regeneration gas stream the catalyst initially showed very rapid deactivation and later was not regenerated to any measurable extent. This demonstrates the desirability, if not the necessity, of having butyl chloride present in the regeneration stream where liquid isobutane, as a representative hydrocarbon, is present along with hydrogen. Separate experiments showed that platinum could be replaced by either 0.5 weight percent palladium or nickel to afford catalysts regenerable under the same conditions as stated above. For both of the latter catalysts the product alkylate had an average RON of about 88.5.

A catalyst of gallium chloride on gamma alumina extrudates containing 0.25 weight percent palladium also was readily regenerable under the stated conditions through at least 8 regenerations without any appreciable loss in activity or stability. Where regeneration was tried only with soluble hydrogen, i.e., hydrogen saturated in liquid isobutane, catalyst stability did deteriorate as evidenced by shorter process cycle times prior to the onset of deactivation.

Catalysts prepared by subliming 1) zirconium tetrachloride, ZrCl$_4$ on alumina containing 0.25weight percent platinum, 2) titaniumtetrachloride, TiCl$_4$ ongammaalumina containing 0.25 weight percent platinum, and 3) aluminum chloride on spherical silicaalumina (75-90 weight percent silica) having 0.25 weight percent platinum were also shown to be regenerable over multiple process cycles. In all cases the product alkylate gave an average RON of 88-89.

Catalysts were prepared of boron trifluoride, BF$_3$, modified alumina with and without 0.25 weight percent platinum. Without platinum the catalyst was not regenerable, while with platinum the catalyst was regenerable for multiple cycles using either this procedure or that of Example 1. In all cases the product alkylate had an average RON of about 91.5.

WHAT IS CLAIMIED IS:

1. A method of regenerating an alkylation catalyst, said catalyst consisting essentially of 1) the reaction product of a first metal halide and the bound surface hydroxyl groups of refractory inorganic oxide and 2) a zerovalent second metal, where said first metal halide is a fluoride, chloride, or bromide and the first metal is selected from the group consisting of aluminum, zirconium, tin, tantalum, titanium, gallium, antimony, phosphorus, and boron and any combination thereof, and said second zerovalent metal is selected from the group consisting of platinum, palladium, nickel, ruthenium, rhodium, osmium and iridium, and any combination thereof, said catalyst having become at least partially deactivated during its catalysis of the liquid phase alkylation of an alkene having from 2 up to 6 carbon atoms with an alkane having from 4 up to about 6 carbon atoms, said method comprising removing all of the liquid phase from the catalyst, treating said catalyst with hydrogen at a partial pressure of from about 1 up to about 2000 psi for a time from about 1 un to about 20 hours, at a temperature from about 10 up to about 300° C. in the presence of liquid alkane and a chloride source and recovering a regenerated catalyst having substantially increased activity.

2. The method of claim 1 where the first metal is selected from the group consisting of aluminum, zirconium, titanium, gallium, boron, and any combination thereof 3. The method of claim 2 where the first metal is aluminum.

4. The method of claim 2 where the first metal is zirconium.

5. The method of claim 2 where the first metal is boron.

6. The method of claim 2 where the first metal is gallium.

7. The method of claim 2 where the first metal is titanium.

8. The method of claim 1 where the second metal is platinum, palladium, or any combination thereof.

9. The method of claim 1 where the second metal is nickel.

10. The method of claim 1 where the catalyst is treated with hydrogen at a temperature from about 10 to about 200° C.

* * * * *

UNITED STATES PATENT AND TRADEMARK OFFICE
CERTIFICATE OF CORRECTION

PATENT NO. : 5,310,713
DATED : MAY 10, 1994
INVENTOR(S) : MASAMI KOJIMA et al.

It is certified that error appears in the above-identified patent and that said Letters Patent is hereby corrected as shown below:

In Column 7, line 27: Change "aluminum$^7$" to --aluminum,--;

line 31: Change "palladium$^7$" to --palladium,--;

In Column 8, line 7: Change "un" to --up--.

Signed and Sealed this

Thirteenth Day of September, 1994

*Attest:*

BRUCE LEHMAN

*Attesting Officer*     *Commissioner of Patents and Trademarks*